United States Patent [19]

Weinert et al.

[11] Patent Number: 5,402,673
[45] Date of Patent: Apr. 4, 1995

[54] SYSTEM FOR TESTING FIRMNESS OF A PAPER ROLL

[75] Inventors: Lawrence E. Weinert, Antioch, Calif.; William C. Glass, Junction City, Oreg.

[73] Assignee: James River Paper Company, Inc., Richmond, Va.

[21] Appl. No.: 245,482

[22] Filed: May 18, 1994

[51] Int. Cl.⁶ .............................. G01N 3/48
[52] U.S. Cl. ........................ 73/82; 73/1 J
[58] Field of Search ........... 73/1 R, 1 J, 81, 82, 73/12.09

[56] References Cited

U.S. PATENT DOCUMENTS

| | | | |
|---|---|---|---|
| 1,830,842 | 11/1931 | Vercombe | 73/82 |
| 3,194,061 | 7/1965 | Sorenson et al. | |
| 3,540,270 | 11/1970 | Wolfer | |
| 3,822,588 | 7/1974 | Knight et al. | |
| 4,116,047 | 9/1978 | Hejkal | 73/81 |
| 4,159,640 | 7/1979 | Leveque et al. | |
| 4,182,163 | 1/1980 | Hoffmeyer | |
| 4,331,026 | 5/1982 | Howard et al. | 73/1 R |
| 4,435,976 | 3/1984 | Edward, Jr. | |
| 4,667,509 | 5/1987 | Tobolski et al. | |
| 4,945,490 | 7/1990 | Biddle, Jr. et al. | |
| 4,956,994 | 9/1990 | Lue | 73/81 |
| 5,062,293 | 11/1991 | Bakirov et al. | |
| 5,079,728 | 1/1992 | Adams et al. | |
| 5,282,382 | 2/1994 | Fiore et al. | 73/82 |

OTHER PUBLICATIONS

Digimatic Heightgage, User's Manuaal; Mitutoyo Corporation.

*Primary Examiner*—Robert Raevis
*Attorney, Agent, or Firm*—Thomas R. Lampe

[57] ABSTRACT

An apparatus and method for measuring the firmness of a paper roll product. The roll product is mounted on a spindle and a plunger is lowered into engagement with the outer peripheral surface of the roll product. A motion detector detects the distance the plunger moves into the roll product under the weight of the plunger and data based on this distance is displayed for viewing by the operator. Calibrating gauges are employed prior to measurement to ensure that a zero reading on the display corresponds to the point at which the plunger initially contacts the roll product outer surface.

7 Claims, 3 Drawing Sheets

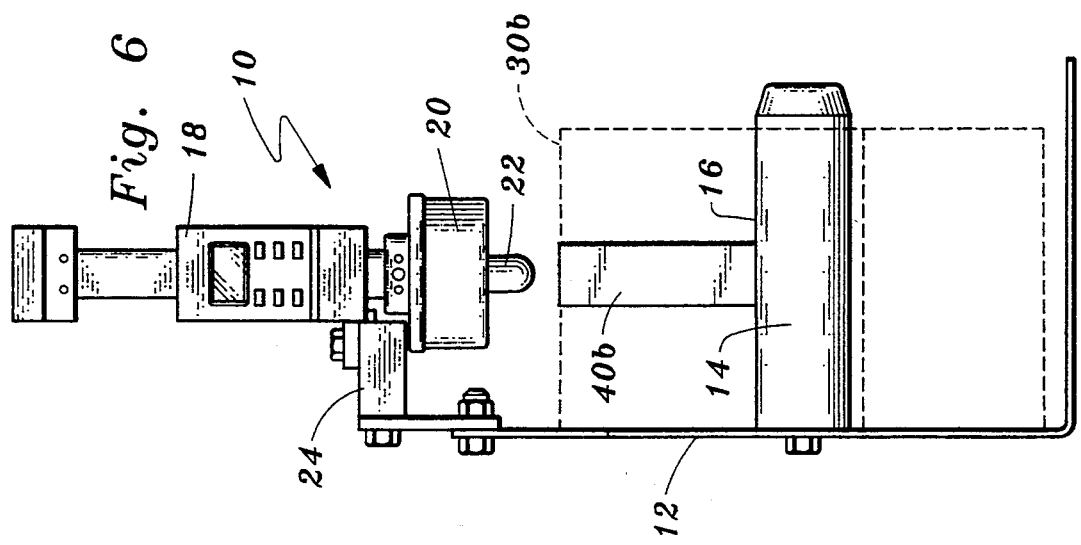
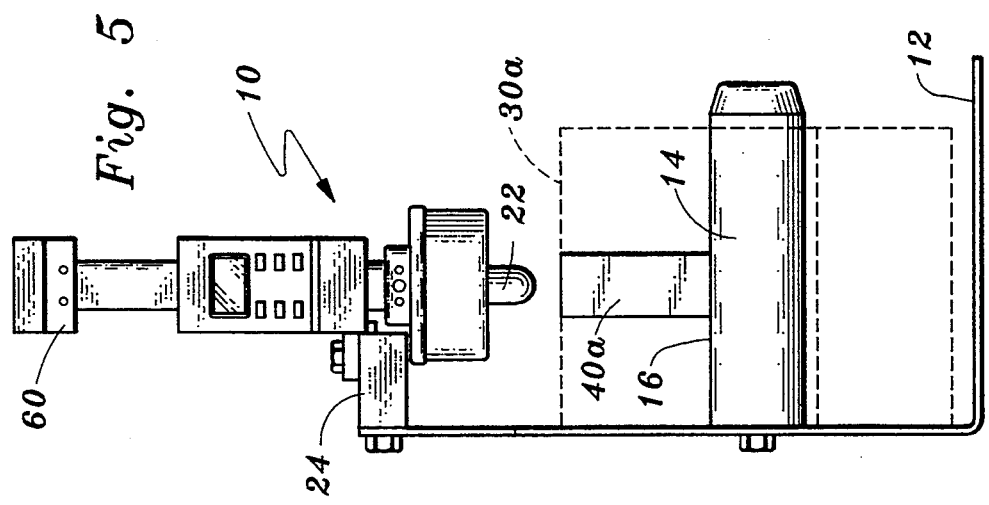
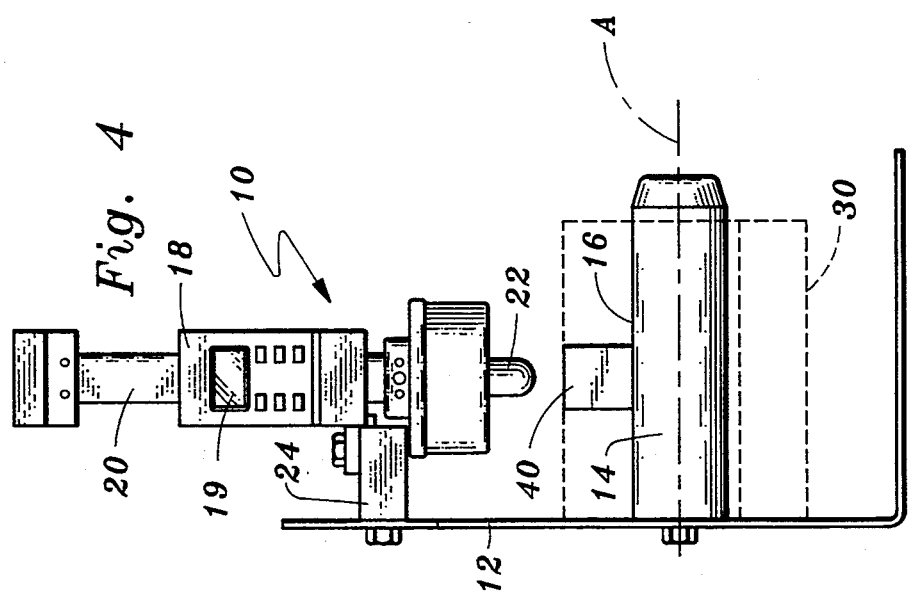

SYSTEM FOR TESTING FIRMNESS OF A PAPER ROLL

TECHNICAL FIELD

This invention relates to apparatus for measuring the firmness of a roll formed from a plurality of convolutions of paper, e.g. tissue. The invention also encompasses a method for measuring the firmness of a roll paper product.

BACKGROUND ART

Many devices are known in the prior art for testing the hardness and/or softness of material. Some prior art systems are for the specific purpose of testing the hardness or softness of paper web material and rolls formed therefrom.

A search of the prior art located the following United States patents: U.S. Pat. No. 3,194,061, issued Jul. 13, 1965, U.S. Pat. No. 4,182,163, issued Jan. 8, 1980, U.S. Pat. No. 3,540,270, issued Nov. 17, 1970, U.S. Pat. No. 4,435,976, issued Mar. 13, 1984, U.S. Pat. No. 4,159,640, issued Jul. 3, 1979, U.S. Pat. No. 5,062,293, issued Nov. 5, 1991, U.S. Pat. No. 4,945,490, issued Jul. 31, 1990, U.S. Pat. No. 5,079,728, issued Jan. 7, 1992, U.S. Pat. No. 3,822,588, issued Jul. 9, 1974, and U.S. Pat. No. 4,667,509, issued May 26, 1987.

It is often desirable to test the firmness of individual rolls of toilet tissue, toweling and the like to provide the manufacturer or others assurance that the roll firmness meets established specifications. The devices disclosed in the patents indicated above are, for the most part, totally inappropriate for such purpose. Furthermore, prior art approaches are characterized by their relative complexity and high expense. In addition, testing of individual rolls is complicated by the fact that such rolls are often produced in different diameters. Differences of diameter must be taken into account when the test is made. The prior art approaches do not address this problem.

DISCLOSURE OF INVENTION

The present invention relates to apparatus for measuring the firmness of a roll formed from a plurality of convolutions of paper. The apparatus is relatively simple and inexpensive as compared to prior art approaches and can readily be utilized to test the firmness of rolls of different diameters.

The apparatus includes a support structure. A spindle is connected to the support structure and projects outwardly therefrom. The spindle has a primary axis, a roll support surface spaced from and above the primary axis, and a distal end.

The apparatus further includes a plunger of a known weight having a roll contact element and a support member for locating the plunger with the roll contact element above the spindle. The plunger is movable relative to the support member and said roll support surface along a linear, vertical path of movement above the spindle and at right angles to the primary axis of the spindle.

Motion detector means is operatively associated with the plunger to detect the distance the plunger moves along the linear, vertical path under the weight of the plunger after engagement of the roll contact element with the outer paper convolution of a roll of paper positioned on the spindle with the spindle within the central roll aperture thereof and the roll of paper on and in engagement with the roll support surface.

Display means displays data based on the distance detected by the motion detector means that the plunger moves along the linear, vertical path under the weight of the plunger after engagement of the roll contact element with the outer paper convolution.

Adjustment means is provided for selectively adjusting the distance between the spindle and the support member to accommodate paper rolls of differing diameters.

The display means includes a digital display for visual read-out of data based on the distance of plunger movement detected by the motion detector means and reset means for setting the display to zero read-out at any one of a plurality of plunger roll contact positions above the spindle.

The method of the present invention is for measuring the firmness of a roll formed from a plurality of convolutions of paper, the roll having an outer convolution defining the outer periphery of the roll and an inner paper convolution disposed about a central roll aperture.

The method includes the step of positioning a roll over a spindle having a primary axis, a roll support surface spaced from and above the primary axis, and a distal end.

The roll is supported on the spindle with the spindle within the central roll aperture thereof and the roll of paper on and in engagement with the roll support surface.

A plunger of known weight having a roll contact element is located above the roll and the spindle.

The roll contact element is brought into engagement with the outer paper convolution of the roll.

The plunger is moved along a linear, vertical path under the weight of the plunger after engagement by the roll contact element with the outer paper convolution of the roll.

Movement of the plunger is terminated when upwardly directed forces exerted on the roll contact element by the roll equal the force of weight of the plunger.

The method also includes detecting the distance the plunger moves along the linear, vertical path after engagement of the roll contact element with the outer paper convolution of the roll until movement is terminated.

Data based on the distance detected during the detecting step is displayed on a display.

Other features, advantages, and objects of the present invention will become apparent with reference to the following description and accompanying drawings.

BRIEF DESCRIPTION OF DRAWINGS

FIGS. 4, 5 and 6 are frontal, elevational views of the apparatus illustrating set-up of the apparatus for measurement of paper rolls of differing diameters.

BEST MODE FOR CARRYING OUT THE INVENTION

Figure 1:
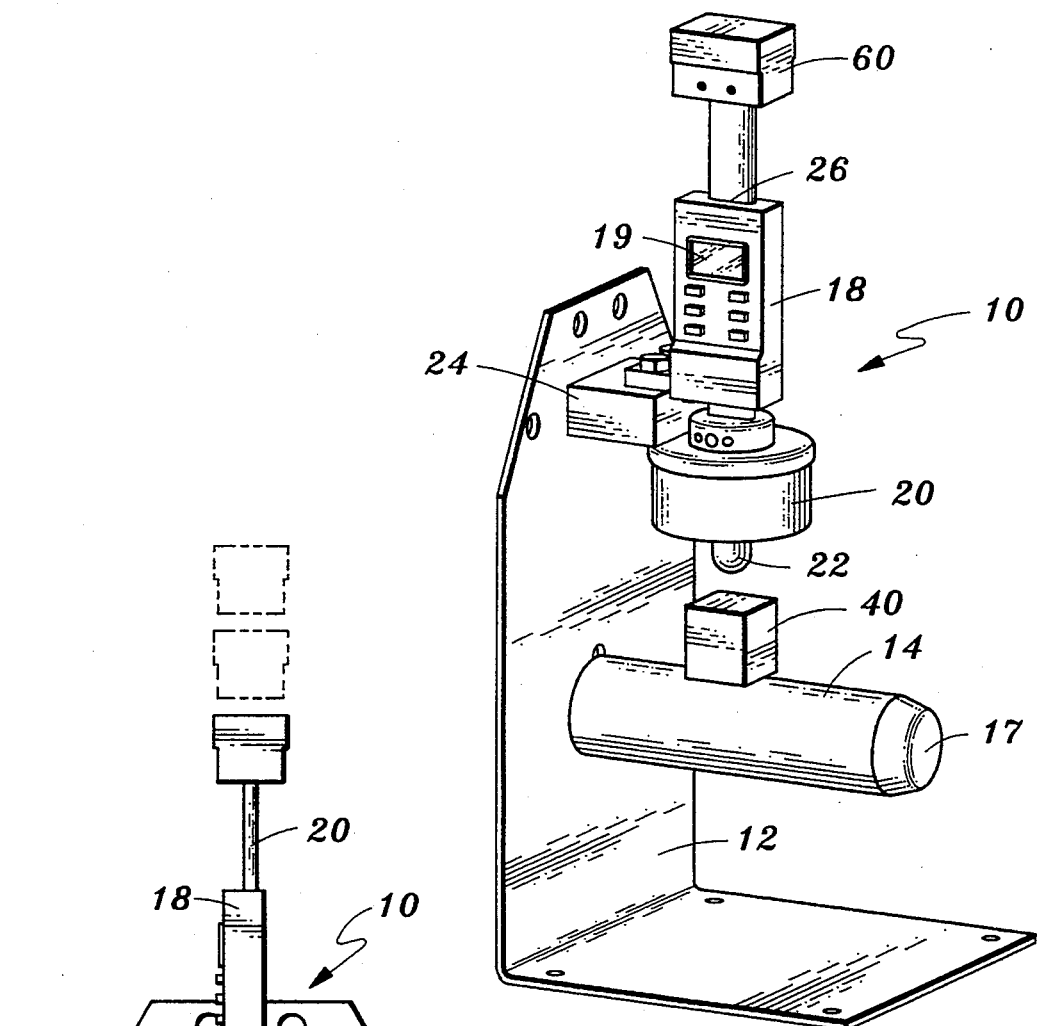
FIG. 1 is a frontal, perspective view of apparatus constructed in accordance with the teachings of the present invention.

Referring now to the drawings, apparatus constructed in accordance with the teachings of the present invention is generally designated by reference numeral 10. Apparatus 10 includes a support structure in the form of a stand 12.

Figure 3:
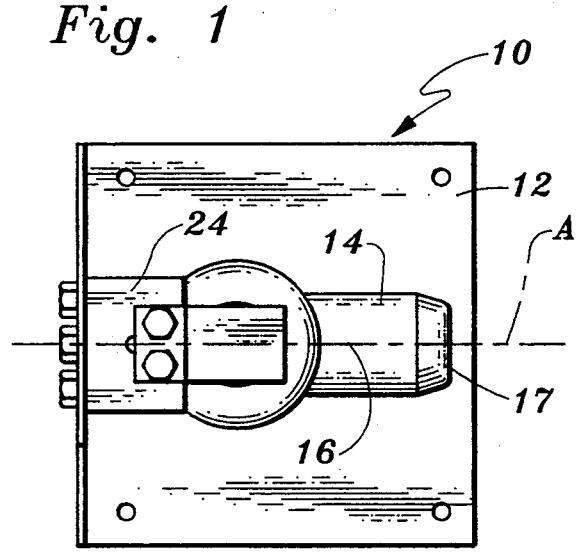
FIG. 3 is a top, plan view of the apparatus.

A spindle 14 is connected to the support structure 12 and projects outwardly therefrom. The elongated spindle has a primary axis A (FIGS. 3 and 4), a roll support surface 16 spaced from and above the primary axis, and a distal end 17.

Connected to frame 12 is a motion detector device 18 having a digital read-out display 19. As will be explained in greater detail below, the motion detector 18 is for the purpose of measuring or detecting the distance of movement of a plunger 20 operatively associated therewith. Plunger 20 has a roll contact element 22 at the bottom end thereof.

A commercially available device has been found suitable for use as the motion detector 18. More particularly, motion detector 18 is a component known as the "slider" of a digital display height measuring gauge made available by MITUTOYO MFG. CO. LTD. of Tokyo, Japan, identified as Digimatic Heightgage 570 series. When functioning as a part of the height gauge just identified, the slider slides along a scale which is located in a slot extending through the slider. The display 19 displays the distance the slider moves along the scale through the use of LCD's. The slider incorporates structure which enables the operator to set the display to zero read-out at any desired relative position between the slider and the scale.

In the apparatus of the present invention, element 18 is not employed as a slider but is fixed in position relative to stand 12 and spindle 14 by a support member 24 secured to the stand by a threaded fastener passing through an aperture in the stand.

Plunger 20 incorporates the scale with which the motion detector device 18 is conventionally employed when utilized as a height measuring gauge. The plunger 20 passes through the slot 26 within the motion detector 18 which conventionally accommodates a scale. That is, with the present approach, the motion detector 18 is fixed and the plunger is movable relative thereto as well as relative to the support member 24 and the roll support surface 16. The movement of the plunger, which is of known weight, e.g. one kilogram, is restricted by the device 18 to a linear, vertical path of movement above the spindle 14 and at right angles to the primary axis A of the spindle.

Motion detector 18 detects the distance the plunger 20 moves along the linear, vertical path under the weight of the plunger. A reset button on the motion detector 18 can be utilized to set a zero read-out at any relative position between the plunger and the motion detector. This feature is utilized in the present invention to calibrate operation of the apparatus to particular roll diameters of the rolls which are to be tested for firmness. As will be seen below, detected motion or length of travel of the plunger after engagement of the roll contact element with the outer peripheral convolution of the roll provides a measure of firmness of the roll.

FIGS. 1 and 7-9, inclusive, illustrate the steps which are carried out when testing the firmness of a roll of tissue 30. The operator already knows the diameter of roll 30. For example, roll 30 may be one of many rolls produced at a particular manufacturing plant manufactured to a single roll diameter specification. Other manufacturing venue specifications may differ with regard to roll diameter as well as with regard to other physical characteristics. Roll 30 is of conventional construction having an outer paper convolution 32 and an inner paper convolution 34 disposed about a central roll aperture. The particular roll illustrated does not have a central core but it is to be understood that the present system is applicable to both coreless rolls and rolls with cores.

Figure 7:
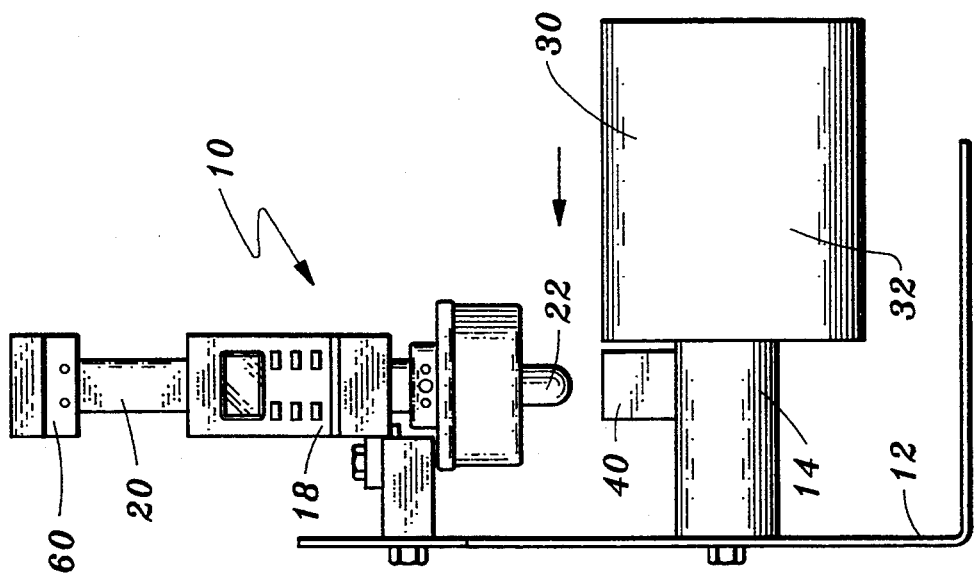

Before positioning roll 30 over spindle 14, the operator places a calibrating gauge member 40 on spindle 14 under plunger roll contact element 22. More particularly, the gauge member 40 is positioned directly on roll support surface 16. This step is illustrated in FIGS. 1 and 7. Prior to placement of the gauge member 40 in position the operator manually pulls plunger 20 upwardly out of the way to provide proper clearance between roll contact element 22 and the gauge member.

Now the operator gently lowers the plunger to bring the roll contact element 22 into contact with the top of the gauge member. The digital read-out display is then set by the operator to zero read-out. As shown in FIG. 7, the distance of the top surface of the gauge member 40 is the distance the roll outermost convolution is above spindle 14 when the roll 30 is slid in position on the spindle. The gauge member has been specifically sized and configured for this based upon the user's prior knowledge of the dimensions of the roll.

Figure 8:
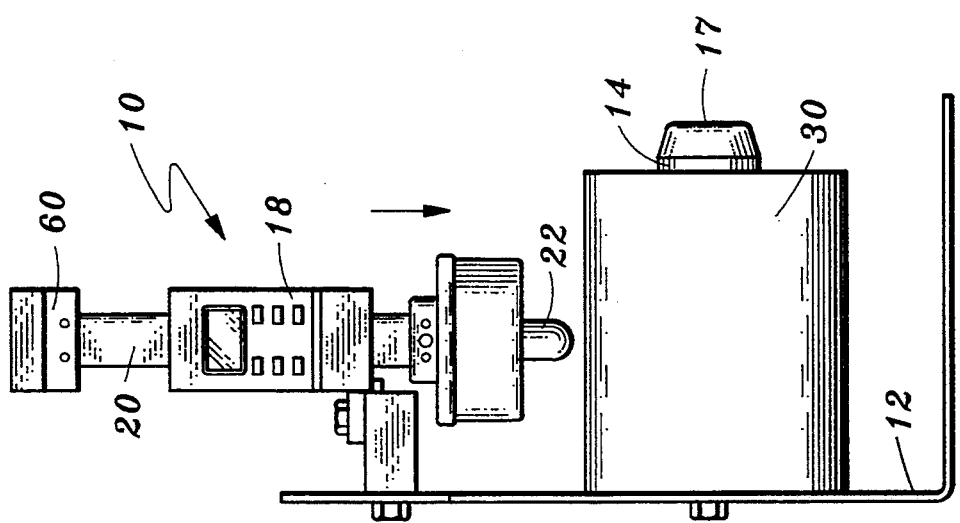

The measuring gauge 40 is removed from the spindle and the roll slid over the spindle as shown in FIGS. 7 and 8, it being understood that the operator previously has manually positioned plunger 20 sufficiently high above the spindle to provide clearance between the roll and roll contact element 22.

Figure 9:
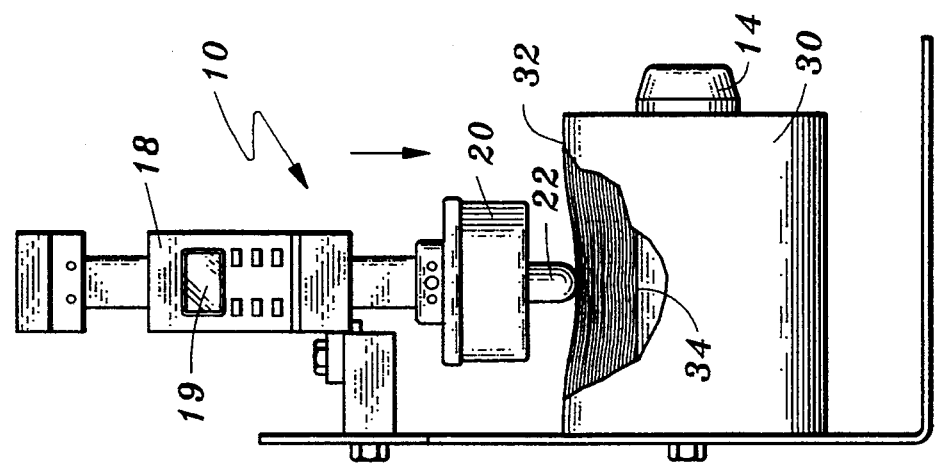
FIGS. 7, 8 and 9 are frontal, elevational views of the apparatus showing sequential stages in the operation thereof when practicing the teachings of the present invention.

Next the operator slowly brings the roll contact element 22 into engagement with the outer periphery of the roll as defined by the outermost convolution thereof. When this occurs, the read-out of digital read-out display 19 will be zero because of the previous calibration made with calibrating gauge member 40. The plunger will now be allowed to move downwardly relative to the roll under its own weight. Movement will continue until the upwardly directed force exerted on the roll contact element by the roll equals the force of the weight of the plunger. This condition is shown in FIG. 9. The operator then reads digital read-out display 19 in millimeters or other appropriate length measurement units, it being understood that the displayed number indicates the firmness of the roll. If desired, the CPU of the detector 18 may be suitably programmed to provide a read-out expressed directly in some firmness value which is a function of plunger movement.

FIG. 5 illustrates the apparatus prior to firmness testing of a roll 30a which has a diameter considerably larger than that of roll 30. Consequently, calibrating the instrument for firmness testing of roll 30a would require a calibrating gauge member 40a which projects upwardly from spindle 14 a greater distance than gauge member 40. It should also be noted in FIG. 5 that the support member 24 has been positioned at a higher level relative to frame 12 than in FIG. 4. An adjustment slot could be provided in the frame for such purpose.

Figure 2:
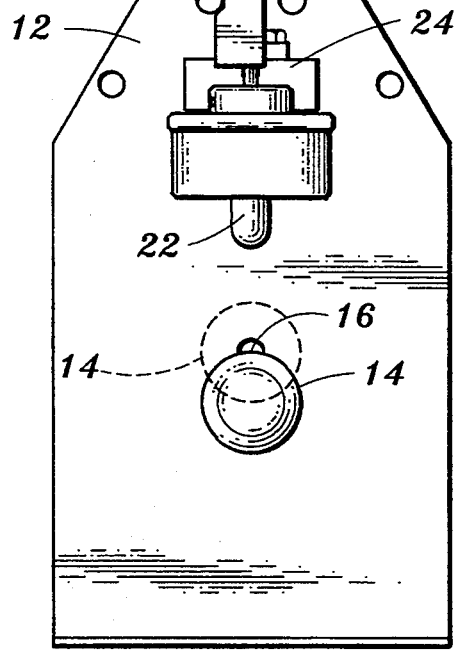
FIG. 2 is a right side, elevational view of the apparatus.

FIG. 6 shows the support member 24 located even higher above spindle 14, an extension arm being used for such purpose. Roll 30b in FIG. 6 is of a greater diameter than either roll 30 or 30a. Likewise, the calibrating gauge member 40b is longer than gauge members 40 or 40a. In FIGS. 4, 5 and 6 the rolls are indicated in phantom line and the corresponding calibrating gauge members 40 in solid line. If desired, the spindle 14 may also be adjustably mounted for up and down movement relative to the frame as shown in FIG. 2.

As indicated above, the plunger is of known weight. The plunger may include a secondary weight 60 to bring the plunger to the desired weight, e.g. one kilogram. Weight 60 can also function as a handle to lift the plunger.

We claim:

1. Apparatus for measuring the firmness of a roll formed from a plurality of convolutions of paper, said roll having an outer paper convolution defining the outer periphery of said roll and an inner paper convolution disposed about a central roll aperture, said apparatus comprising, in combination:
   a support structure;
   a spindle connected to said support structure and projecting outwardly therefrom, said spindle having a primary axis, a roll support surface spaced from and above said primary axis, and a distal end;
   a plunger having a roll contact element;
   a support member for locating said plunger with the roll contact element above said spindle, said plunger being movable relative to said support member and said roll support surface along a linear, vertical path of movement above said spindle and at right angles to the primary axis of said spindle;
   motion detector means operatively associated with said plunger to detect the distance said plunger moves along said linear, vertical path under the weight of said plunger after engagement of said roll contact element with the outer paper convolution of a roll of paper positioned on said spindle with the spindle within the central roll aperture thereof and said roll of paper on and in engagement with said roll support surface;
   display means for displaying data based upon the distance detected by said motion detector means that the plunger moves along said linear, vertical path under the weight of said plunger after engagement of said roll contact element with the outer paper convolution, said display means including a digital display for visual read-out of the distance of plunger movement detected by said motion detector means and reset means for setting said display to zero read-out at any one of a plurality of plunger roll contact element positions above said spindle; and
   calibrating gauge means positionable between said spindle and said plunger roll contact element to support the weight of said plunger on said calibrating gauge means and on said spindle roll support surface and locate the plunger roll contact element at a plunger roll contact element position a fixed predetermined distance above said spindle roll support surface whereby said display may be set to zero read-out when the plunger roll contact element is at said fixed predetermined distance above said spindle roll support surface.

2. The apparatus according to claim 1 additionally comprising adjustment means for selectively adjusting the distance between said spindle and said support member to accommodate paper rolls of differing diameters.

3. The apparatus according to claim 2 wherein said motion detector means slidably receives said plunger and restricts movement of said plunger to said linear, vertical path.

4. The apparatus according to claim 3 wherein said support member is connected to said motion detector means and supports said motion detector means.

5. The apparatus according to claim 1 wherein said calibrating gauge means comprises a plurality of calibrating gauge members alternatively positionable between said spindle and said plunger roll contact element to support the weight of said plunger and locate the plunger roll contact element at different fixed predetermined distances above said spindle roll support surface whereby said display may be set to zero read-out when the plunger roll contact element is at each of said fixed predetermined distances above said spindle roll support surface.

6. A method for measuring the firmness of a roll formed from a plurality of convolutions of paper, said roll having an outer convolution defining the outer periphery of said roll and an inner paper convolution disposed about a central roll aperture, said method comprising the steps of:
   positioning a roll over a spindle having a primary axis, a roll support surface spaced from and above the primary axis, and a distal end;
   supporting the roll on said spindle with the spindle within the central roll aperture thereof and said roll of paper on and in engagement with said roll support surface;
   locating a plunger having a roll contact element above said roll and said spindle;
   bringing the roll contact element into engagement with said outer paper convolution of said roll;
   moving said plunger along a linear, vertical path under the weight of said plunger after engagement of said roll contact element with the outer paper convolution of said roll;
   terminating movement of said plunger when the upwardly directed force exerted on said roll contact element equals the force of weight of said plunger;
   detecting the distance the plunger moves along said linear, vertical path after engagement of said roll contact element with the outer paper convolution of said roll until movement is terminated;
   displaying data based on the distance detected during said detecting step on a display;
   inserting a calibrating gauge between the spindle and the plunger; and
   bringing the spindle and plunger into simultaneous contact with the calibrating gauge while the calibrating gauge is between the spindle and plunger prior to the step of positioning the roll over said spindle, the height of said calibrating gauge and the distance between the spindle and plunger while in simultaneous contact with the calibrating gauge being equal to each other and to the distance between the roll support surface and the outer convolution of the roll to be positioned over the spindle.

7. The method according to claim 6 additionally comprising setting the read-out of said display to a zero reading while the calibrating gauge is between and in engagement with the spindle and plunger, and removing the gauge from the spindle after the read-out of said display is set to a zero reading.

* * * * *